United States Patent [19]
Cook et al.

[11] Patent Number: 5,725,516
[45] Date of Patent: Mar. 10, 1998

[54] SUCTION CANISTER SYSTEM

[75] Inventors: Charles Cook, Whitehouse; David G. Garber; Steven B. Sanford, both of Jacksonville, all of Tex.; Phillip M. Summers, Kenner, La.

[73] Assignee: Allegiance Healthcare Corp.

[21] Appl. No.: 486,021

[22] Filed: Jun. 7, 1995

Related U.S. Application Data

[63] Continuation-in-part of Ser. No. 86,782, Jul. 1, 1993, Pat. No. 5,470,324.
[51] Int. Cl.⁶ .................................................. A61M 1/00
[52] U.S. Cl. .................................. 604/319; 128/760
[58] Field of Search .............................. 604/317–323, 604/326, 324, 325; 128/760

[56] References Cited

U.S. PATENT DOCUMENTS

| | | |
|---|---|---|
| 3,863,664 | 2/1975 | Holbrook et al. . |
| 3,913,780 | 10/1975 | Holbrook et al. . |
| 3,938,540 | 2/1976 | Holbrook et al. . |
| 4,013,076 | 3/1977 | Puderbaugh et al. . |
| 4,275,732 | 6/1981 | Gereg . |
| 4,379,455 | 4/1983 | Deaton . |
| 4,384,580 | 5/1983 | Leviton . |
| 4,388,922 | 6/1983 | Telang . |
| 4,397,643 | 8/1983 | Rygiel . |
| 4,430,084 | 2/1984 | Deaton . |
| 4,465,483 | 8/1984 | Weilbacher . |
| 4,475,904 | 10/1984 | Wang . |
| 4,642,105 | 2/1987 | Toter . |
| 4,681,571 | 7/1987 | Nehring . |
| 4,772,278 | 9/1988 | Baber . |
| 4,826,494 | 5/1989 | Richmond et al. ............ 604/323 |
| 4,877,219 | 10/1989 | Yano . |
| 4,986,292 | 1/1991 | Rieple .......................... 137/348 |
| 5,011,470 | 4/1991 | Kurtz et al. . |
| 5,045,077 | 9/1991 | Blake, III . |
| 5,141,504 | 8/1992 | Herweck et al. . |
| 5,149,325 | 9/1992 | Telang et al. . |
| 5,185,007 | 2/1993 | Middaugh et al. . |
| 5,318,548 | 6/1994 | Filshie . |

FOREIGN PATENT DOCUMENTS

| | | |
|---|---|---|
| PCT/GB89/00424 | 2/1990 | WIPO . |
| PCT/US94/07257 | 6/1994 | WIPO . |

*Primary Examiner*—John G. Weiss
*Assistant Examiner*—Dennis Ruhl
*Attorney, Agent, or Firm*—Oppenheimer Poms Smith

[57] ABSTRACT

A patient fluid collection system is disclosed which includes a fluid collection reservoir, a cover for the reservoir, and a port on the reservoir having a scalloped upper edge. The scalloped upper edge prevents the port from being inadvertently closed off in the event that a tube valve containing a flapper valve is improperly positioned on the port.

23 Claims, 9 Drawing Sheets

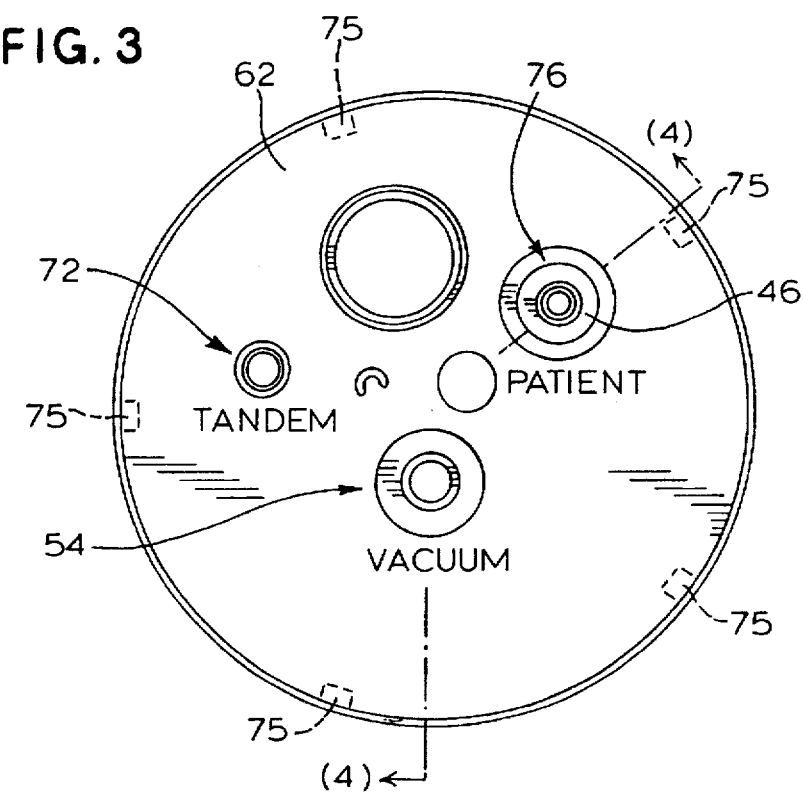
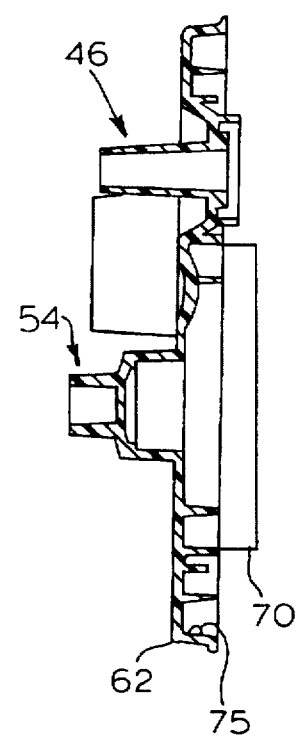
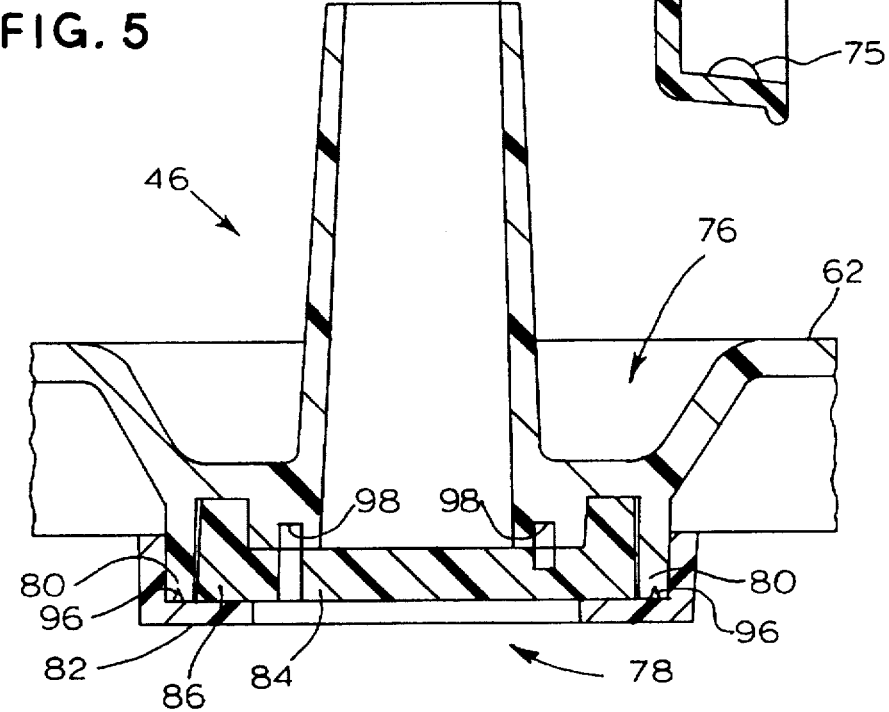

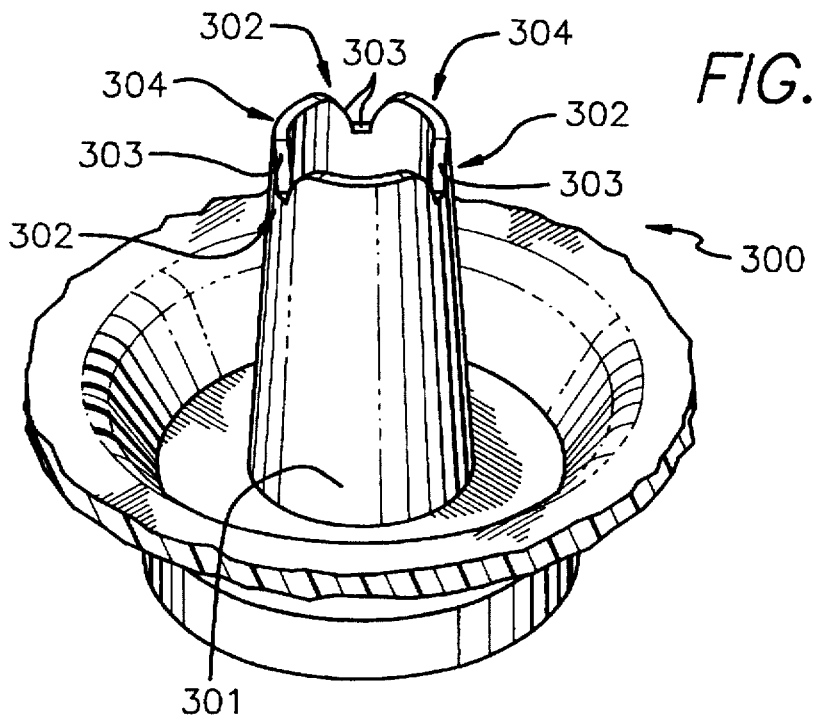
FIG. 20
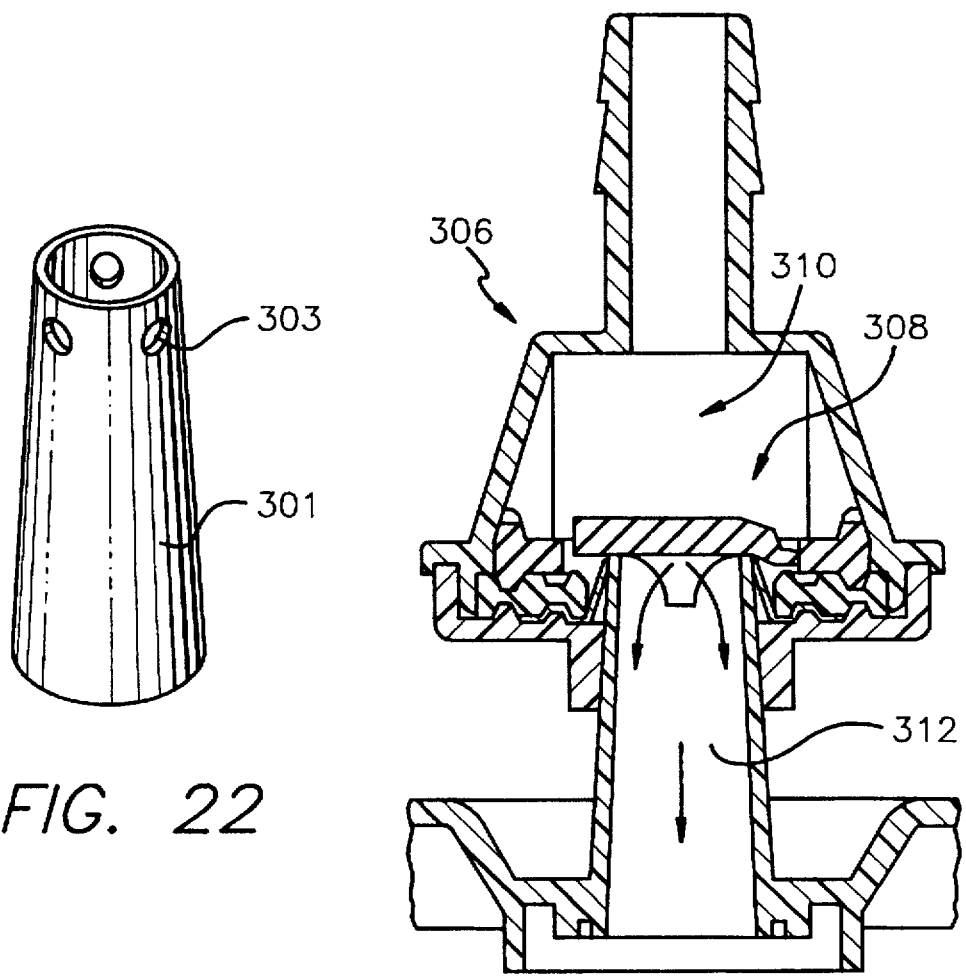
FIG. 21
FIG. 22

SUCTION CANISTER SYSTEM

CROSS REFERENCE TO RELATED APPLICATIONS

This application is a continuation-in-part of application serial number 08/086,782, filed Jul. 1, 1993 and now Pat. No. 5,470,324, incorporated herein by reference.

BACKGROUND OF THE INVENTION

1. Field Of The Invention

The present invention relates to non-refluxing suction canister systems and components therefor, and more specifically to such systems having canisters closed by anti-refluxing valves or which have flexible liners.

2. Related Art

During operative surgery and other medical and biological procedures, suction canister systems are used to collect fluids from a patient, including blood, saline, and any other fluids which may accumulate or must be removed and contained during the procedure and disposed of after the procedure. The collection system uses suction canisters and a vacuum source. While a single canister can be and are often used, a multiple canister suction system will be described because the use and operation of a single canister system is apparent from that for a multiple system. Multiple canisters are arranged in tandem with a first canister having a suction tube to collect fluids from a source and to deposit the fluids in the first canister. Downstream canisters are coupled together with their vacuum sources applied in series or in parallel from a vacuum source connected at the end canister.

Typically, a canister unit includes an open-top cylindrical canister closed by a cover or lid to which is sealed an internal liner to be contained in the canister. Vacuum is applied through the canister wall to the space or cavity between the liner and the canister wall to expand the liner outwardly into contact with the canister wall. Vacuum is also applied for each canister to a vacuum port in the lid to develop a subatmospheric pressure or vacuum within the liner, which vacuum then also develops at the collection tube at the desired level. Tandem tubes connect the interior of the liner of the first canister to the inlet port on the lid of the next succeeding canister so that when the first canister fills, fluid in the first canister thereafter passes to the second canister, and so on.

The lid typically includes several access ports with associated attachment or connection elements. A vacuum port accepts a tube from the vacuum source to apply vacuum internal to the liner. An inlet or patient port accepts one end of the suction tube. A large access port is typically capped until a fluid setting agent such as Isolizer is to be added. An outlet or "ortho" port includes a wider riser portion than the patient port for connection of a suction tube during orthopaedic operations or for connection of a tandem tube for connecting an additional collection canister to the first. The vacuum port of each canister includes a float valve to prevent withdrawal of fluids into the vacuum system. However, the other ports in the lid which are exposed to the fluids lack any vane and are subject to reflux and may lead to contamination of personnel or a working area.

In situations where one or more canisters become filled before the end of the procedure, fluid may reflux or come out of one or more ports under certain circumstances. For example, if vacuum is removed from the system, the pressure differential between atmosphere on the one hand and the cavity between the canister and the lining one the other, created by the vacuum between the canister and the liner, is removed. Removal of the vacuum allows the liner to collapse somewhat, due to liner elasticity, increasing the internal pressure on the fluid inside the liner. This increased pressure could cause fluid to be pushed out through the suction tube toward the patient or otherwise out the collection tube. Fluid may also be pushed out the port for the tandem tube toward a secondary canister. When the interconnected canisters are disconnected, fluid may be ejected from the tandem tube, thereby possibly contaminating surfaces or personnel.

As a further result of the increased liner pressure differential, the canister liner may still be sufficiently enlarged or inflated to remain in contact with the walls of the canister, making it difficult to withdraw the lid and liner from the canister, for the similar reason as it is difficult to remove a filled plastic bag from a trash can. To remove the lid and liner, personnel often try to manipulate the lid and liner either by grasping the liner or grasping fittings on the lid to gain an advantage in forcibly removing the lid and liner from the canister. Such manipulation often puts pressure on the liner thereby increasing the tendency of the liner to eject fluid, and also places force on the fittings which could cause removal of caps on fittings or breakage of fittings, connections or caps. Each of these could cause contamination through ejection of fluids.

One or more flapper valves may be used in a vacuum collection system to close off openings, as desired, such as after a tube is removed from a port or spout. A flapper valve may typically include a natural rubber disc for covering the opening, which may be resiliently biased or normally positioned closed, but held open during operation of the system by the port, spout or some other element. In the suction cannister configuration, the element holding the flapper valve open may be the spout or port with which the valve is associated. For example, the flapper valve may be internal to a connector fitted over an upstanding spout, and the upstanding portion of the spout contacts the disc of the flapper valve to move it out of the way of the opening. Occasionally, however, the connector may not be fully positioned on the spout and the disc may not be sufficiently moved away from the opening. In a vacuum system, a pressure differential may exist across the disc, and if the disc is not fully moved out of the opening, the pressure differential may be high enough to push the disc back toward the opening and possibly shut down the vacuum system or restrict flow through the opening.

As long as vacuum is applied to the system, equilibrium should exist throughout the system. However, once vacuum is removed or once vacuum is removed and personnel attempt to dismantle the system to dispose of the filled liners, the possibility of contamination increases. There exists, therefore, a need for a system which further minimizes the possibility of loss of fluid or contamination in vacuum collection systems.

SUMMARY OF THE INVENTION

The present invention provides a fluid collection system which reduces the possibility that the system is shut down or that suction through a valve is reduced to an unacceptably low level. In one preferred embodiment, a suction canister includes a suction port to which a connector with a valve is associated where the port includes a passageway that minimizes the possibility that the system is shut off by inadequate installation of a valve over the suction port. More specifically, in one preferred form of the invention, the patient suction port on a suction canister includes discontinuities or other air passageways near its upper rim, such that even if a flapper valve within a tube valve comes down over the rim because of a pressure differential across the valve, the air passageways allow air to flow into the suction port, thereby preventing the flapper valve from cutting off air flow through the patient suction port.

In a preferred embodiment, the discontinuities in the patient suction port rim are three scallop-like portions with spaces therebetween. The spaces provide the passageways allowing air to flow into the patient suction port. The rounded scalloped edges allow the flapper valve to contact the top rim of the patient suction port without being damaged thereby.

The present inventions will be demonstrated by the drawings and the detailed description of the preferred embodiments, which follow.

BRIEF DESCRIPTION OF THE DRAWINGS

FIG. 3 is a top plan view of a lid for use with a canister such as shown in FIG. 2.

FIG. 4 is a partial vertical section of the lid of FIG. 3 taken along lines 4—4 showing the vacuum port and patient port.

FIG. 4A is a partial section of a portion of the lid showing a closure clip or bump for the lid.

FIG. 5 is a cross-section of a patient valve with the lid in accordance with one aspect of the present invention.

FIG. 20 is a perspective view of one aspect of a patient suction port of the present invention.

FIG. 21 is a cross-section of one aspect of a patient suction port, with the tube valve and connector insufficiently installed over the suction port.

FIG. 22 shows an embodiment of the suction port where the surface that allows the passage of air from one side of the port to the other is distinct from and is in spaced relation to the port rim.

DETAILED DESCRIPTION OF THE PREFERRED EMBODIMENTS

In accordance with the present invention, a fluid collection system is provided which takes full advantage of pressure differentials created in the fluid collection system to increase the integrity of the system and its component parts, and to reduce the possibility of contamination through fluid loss or reflux. The system of the present invention provides a more secure system and provides lid and liner combinations which are more easily neutralized and disposed of.

Figure 1:
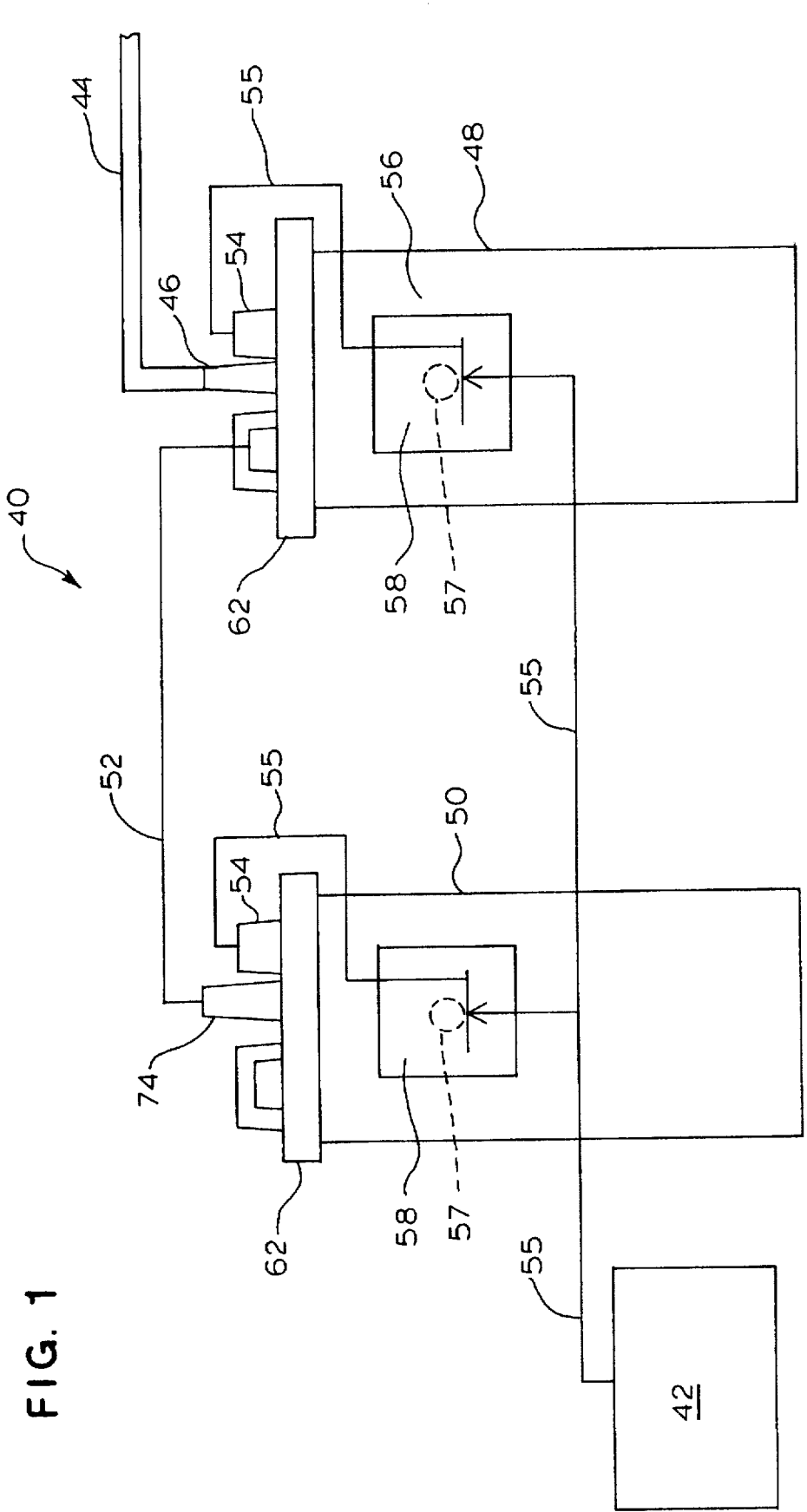
FIG. 1 is side elevation view of a vacuum canister fluid collection system for use with the present invention.

In accordance with the present invention, a vacuum canister fluid collection system 40 (FIGS. 1 and 2), such as may be used for collecting fluids from patients or other sources during operations, medical procedures or other uses, includes a vacuum source such as pump 42 and a collection tube 44 for collecting fluid from the patient or other source. The collection tube is coupled to the patient port 46 in a first vacuum canister 48, described more fully below. The first canister 48 is fluidly coupled to a second canister 50 through a tandem tube 52. The vacuum pump 42 is also coupled to a vacuum port 54 on the second canister 50 for providing the required pressure differential, as is known to those skilled in the art. Additional suction canisters may be provided as necessary. The vacuum may be applied to the canisters in series or in parallel, as is also known to those skilled in the art. Either arrangement is equally applicable to the present inventions.

In the preferred embodiment, vacuum is also applied to the canister through the canister wall 56 through a vacuum attachment 58 mounted to the outside of the canister wall. Such a configuration is commonly used with the Baxter Medi-Vac CRD flex canister system whereby vacuum is applied to the canister through the vacuum attachment 58 and also to the interior of the liner through the vacuum port 54.

Figure 19:
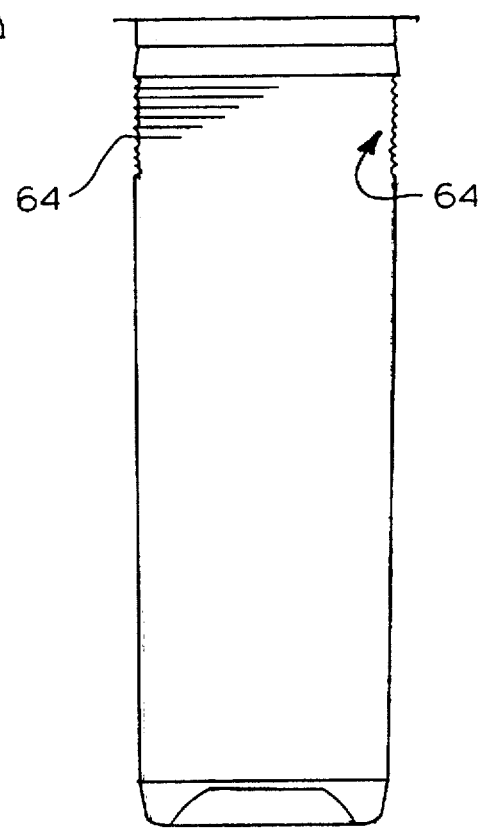
FIG. 19 is a cross-sectional view of a pleated liner for a canister in accordance with the present invention.

Each canister includes a flexible liner 60 fixedly and fluidly sealed within a circular groove formed in the bottom of the lid 62 so that the lid and the liner form a complete and closed container, except for the ports described more fully below. The liner preferably includes an enlargeable or expandable wall portion 64 which (FIG. 19) can expand if the liner fills with fluid such that the effective internal volume of the liner can increase. With this configuration, the liner with an unexpanded but expandable section preferably forms the standard volume for receiving fluid, for a given canister size. If the liner fills with fluid to the standard full volume, the expandable portion 64 can then expand to effectively increase the total volume of the liner. The increased volume preferably reduces any differential pressure between the interior of the lining and ambient pressure when vacuum is removed from the system. The increased liner volume also permits addition of other fluids or materials, such as solidifying agents for the fluid.

In the preferred embodiment, the expandable wall portion is formed from a series of pleats or bellows. Preferably, each pleat is formed circumferentially around the entire circumference of the liner at a location near or adjacent the lid. The series of pleats are preferably formed axially with respect to each other so that the wall portion of the liner can expand or enlarge axially or longitudinally to relieve any pressure differential that may exist when the system is dismantled. Circumferential pleats are preferred over longitudinal pleats because longitudinal pleats may expand even while vacuum is present in the canister and may make it more difficult to remove the liner from the canister.

In the preferred embodiment, for a 3000 ml canister, the enlargeable wall portion may permit addition of 400–600 mls of volume to the liner. It has been found that the pressure differential of conventional liners could result in reflux of approximately 250 ml of fluid at maximum vacuum. By providing about one-fifth or one-sixth again as much additional volume, the additional liner volume may accommodate the pressure differential, as well as accommodate addition of materials for solidifying or otherwise neutralizing the fluid.

Preferably, the pleats are uniform and extend completely around the circumference of the liner, for each pleat. The pleats preferably have a wave length of approximately 0.166 inch, each crest having a preferred radius of approximately 0.015 inch and each trough, extending inward relative to the liner, having a preferred radius of approximately 0.030 inch for a typical liner wall thickness of 0.010 inch.

Figure 2:
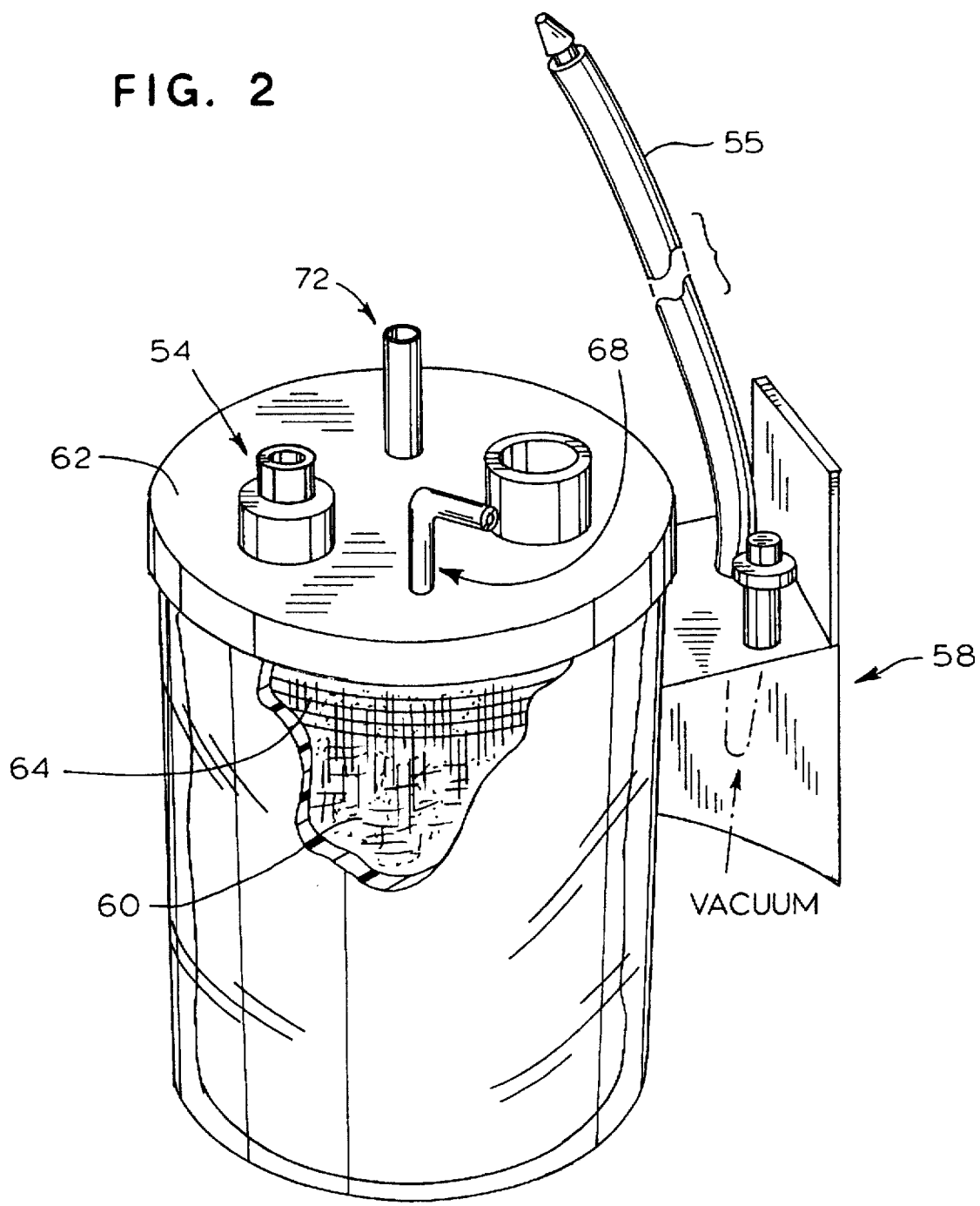
FIG. 2 is a perspective view of a canister for use with the fluid collection system of the present invention.
Figure 6:
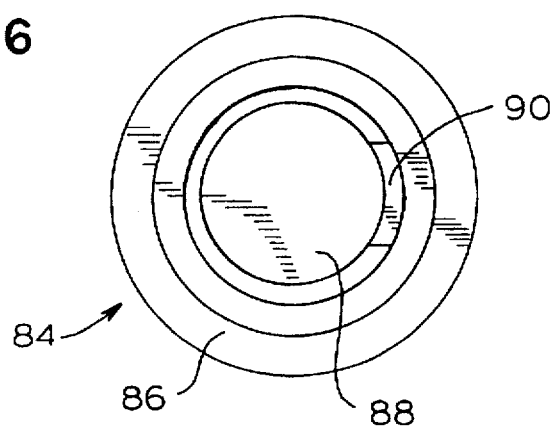
FIG. 6 is a plan view of a flapper valve for use with the patient port.
Figure 7:
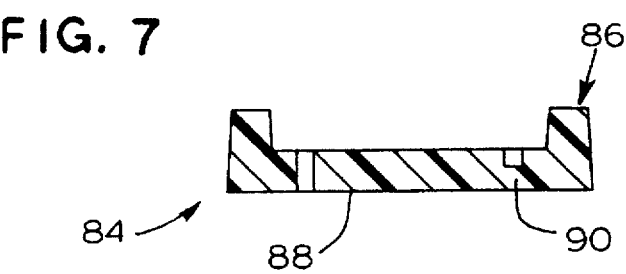
FIG. 7 is a cross-sectional view of the lid flapper valve of FIG. 6.
Figure 8:
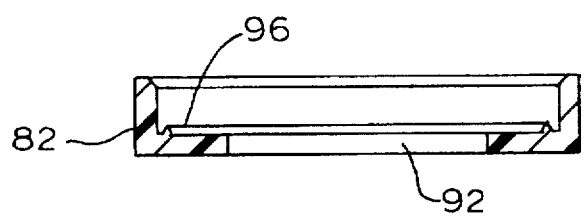
FIG. 8 is a cross-sectional view of a retainer for the lid flapper valve of FIG. 6.
Figure 9:
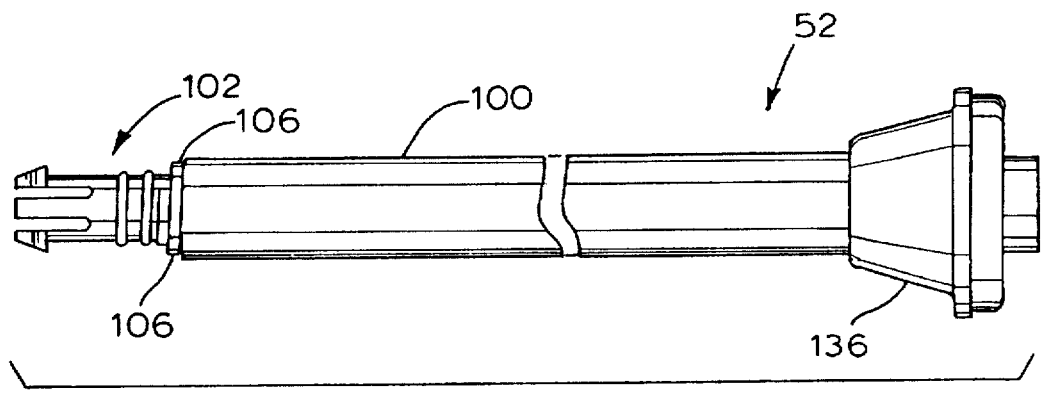
FIG. 9 is a view of a tandem tube in accordance with a further aspect of the present invention.
Figure 10:
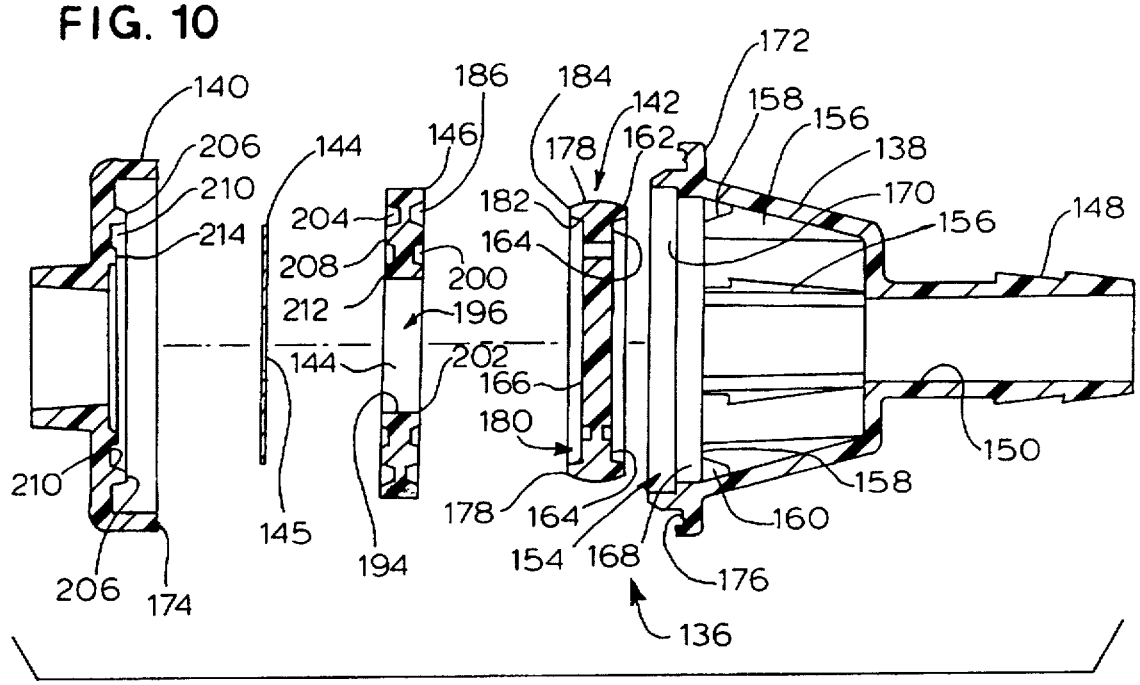
FIG. 10 is a longitudinal cross-section of a tandem tube valve in an exploded configuration.

In operation, vacuum is applied to the cavity or spacing between the canister wall and the liner, and the lid is held in place on the rim of the canister to form an appropriate seal, as is known to those skilled in the art. With the evacuation of the cavity between the liner and the canister walls, the wall of the liner expands flexibly outward into contact with the canister wall to provide a portion of the vacuum for suction and to preclude collapse of the liner wall, as is also known to those skilled in the art. The vacuum system pulls fluid into the interior of the liner through the patient port 46 (FIGS. 3 and 4) and into the volume defined by the liner (FIG. 2). When the liner is full, a conventional float valve 70 attached to the bottom of the vacuum port 54 closes, removing vacuum to the interior of the liner from that port. Thereafter, continued suction results from vacuum applied to the liner in the second canister, which then brings fluid from the liner in the first canister out through the tandem port 72 through the tandem tube 52 and into the liner of the second vacuum canister 50 (FIG. 1) through its respective patient port 74.

When the operation or procedure is complete, the tandem tube is removed from the second canister 50, the vacuum tube is removed from the vacuum port on the lid 62, and also from the vacuum attachment 58. The vacuum port and the other ports on the lid 62 are capped (not shown), as is the free end of the tandem tube. Upon removal of a vacuum from the vacuum attachment 58, the pressure differential between the liner and the canister walls approaches zero, in other words the pressure in the cavity approaches ambient pressure. Because of the earlier vacuum, and influx of fluid into the liner, the fluid pressure within the liner exceeds ambient pressure. This resulting pressure differential exerts an expansive force on the liner and lid. Any expansive forces in the radial or downward direction are retained or contained by the canister wall and bottom surface. However, the only element containing the pressure against the lid is any seal or interference snap fit which may exist between the lid and the rim of the canister after vacuum is removed. The pressure differential is sufficient to break the lid-rim connection, and the internal fluid pressure within the liner presses against the lid and creates a force expanding the pleats, with a resultant increase in liner volume, which is accommodated by movement of the lid upward away from the rim of the canister. Expansion continues until the internal pressure of the fluid is counterbalanced by the return force provided by the flexible material of the liner. It has been found that the internal liner pressure is sufficient after removal of the vacuum to force the lid off of the rim of the canister to allow the liner to continue to expand upwardly. It has also been found that the conventional lid design was sufficient to permit the lid to lift off of the rim, without redesign. However, it was also found that the five clips or bumps evenly distributed about the internal circumferential wall of the lid needed to be moved downward, as viewed in FIG. 4, because repeated flexing of the original lid with vacuum caused the clips to gradually walk up the rim of the canister. The clips were also enhanced to give more of a snap action.

In the preferred embodiment, the patient port on the lid 62 is preferably enlarged to be approximately the same size as the preexisting "ortho" port used with orthopaedic surgical applications. The patient port well 76 is also enlarged to accommodate the larger port cone or riser and connectors, as necessary. The patient port riser may accommodate elbow adaptors and other connectors, as is known to those skilled in the art.

The patient port, in accordance with a further aspect of the present invention, includes a one-way valve 78 mounted to the underside of the lid 62 to allow fluid into the liner and to prevent fluid from exiting the liner through the patient port (FIGS. 5–8).

As shown in FIG. 5, the patient port is slightly tapered to a narrower opening for accepting the collection tube 44, in the case of the first collection canister, or for accepting the tandem tube valve in the case of the second or other vacuum canisters. A circular wall 80 extends downwardly from the underside of the lid to the interior of the liner for accepting, on the outside thereof, a flapper valve housing 82 and for accepting, within the interior thereof, a flapper valve 84. The flapper valve (FIGS. 6 and 7) is preferably a unitary polyisoprene material having an outer ring 86 surrounding an inner moveable valve element 88 substantially in the shape of a circle except for a web 90 connecting the valve element 88 to the outer ring 86. The outer dimension of the valve element 88 is less than the inner dimension of the outer ring 86 so as to form a space for permitting movement of the valve element and fluid flow through the outer ring 86.

The flapper valve housing 82 (FIG. 8) is preferably cup-shaped with a circular opening 92 through which the valve element 88 can extend to permit fluid flow through the flapper valve and into the interior of the liner. The housing 82 fits over and around the downwardly extending wall 80. The fit is facilitated by a chamfer. The radial portion of the housing includes a weld ring 96 extending upwardly toward the circular wall 80.

The flapper valve prevents reflux of fluid from interior to the liner along the passageway of the collection tube 44. Additionally, the flapper valve inhibits fluid flow through the collection tube when the valve is closed, such as after the vacuum has been removed. As a result, reflux of fluid from the open end of the collection tube is minimized. The wider patient port permits use of the fluid collection system in orthopaedic as well as other surgical and medical uses without having to go to another system. The larger port permits easy passage of particulate material which may be passing through the collection tube 44.

In the preferred embodiment, the other side of the patient port includes an annular groove 98 having an inside wall equal to or slightly smaller than the outer dimension of the moveable valve element 88, to ensure proper seating of the valve element against its seat.

In the use of a single suction canister, the tandem port is securely capped to prevent any fluid leakage out the tandem port. What was conventionally the orthopaedic port has been modified to form the tandem port, approximately the same diameter as the inlet or patient port, but having a shorter tapered cone than was ordinarily used with the orthopaedic port. The inside diameter of the port is slightly larger to accept the tandem connector, when used, to fix the tandem tube 52 to the lid. The opposite end of the tandem tube is mounted with the tandem valve, described more fully below.

Figure 15:
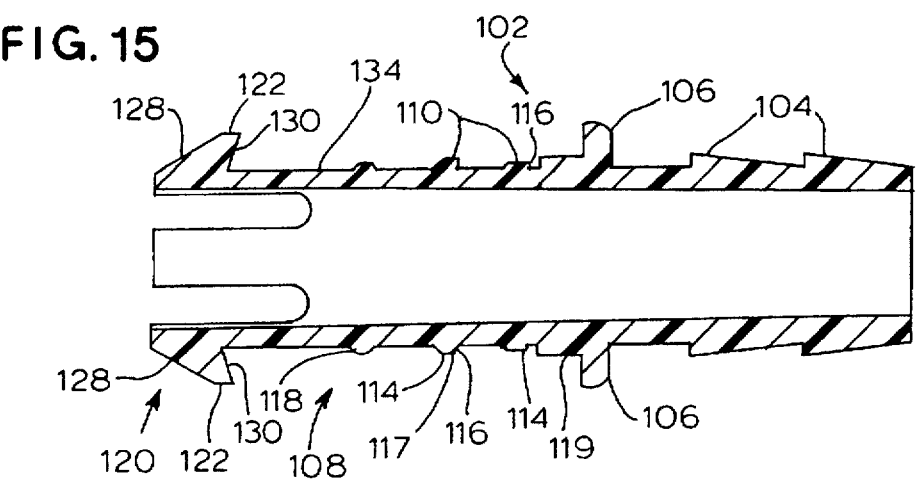
FIG. 15 is a longitudinal cross-section of a tandem tube connector.
Figure 16:
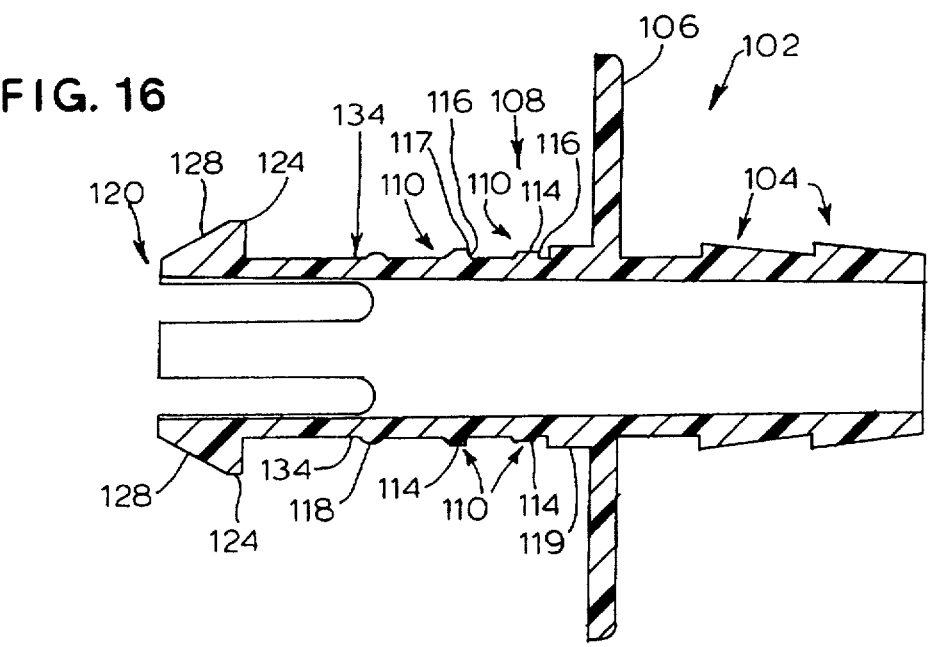
FIG. 16 is a further cross-section of the tandem tube connector rotated about a longitudinal axis approximately 90 degrees from the view shown in FIG. 16.
Figure 17:
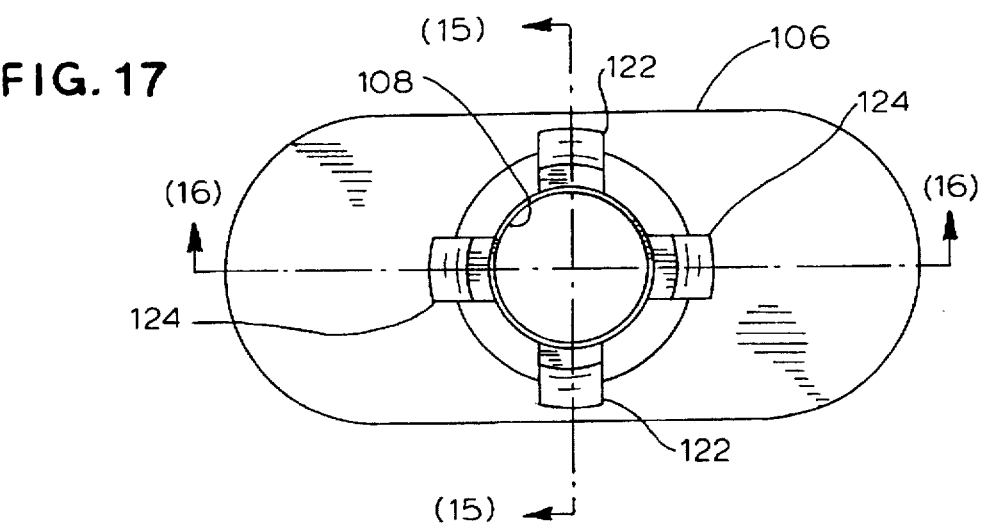
FIG. 17 is a bottom plan view of the tandem tube connector.

The tandem tube 52 includes a flexible tube 100 mounted to the tandem connector 102 through an interference fit over ribs 104 (FIGS. 15 and 16). The interference fit is sufficient to prevent removal of the tube from the connector by hand. The tandem connector 102 includes wings 106 to serve as a stop to prevent the connector from being inserted into the tandem port further than the stop and also to provide a surface for applying pressure on the connector to press it into the tandem port. The tandem tube connector has a body 108 preferably cylindrical in general outline with one or more circumferential ridges or coupler rings 110 to form a seal between the tandem connector body and the interior wall of the tandem port when the connector is fully seated in the port. The lower portion of each ridge 110 slants upwardly and outwardly from the body to a flat circumferential wall 114 which engages the interior wall of the port. Each ring terminates at a flat surface 116 extending from the circumferential wall 114 back to the body 108. The distal-most ring includes an outwardly extending flange 117 extending circumferentially around the proximal-most portion of the wall 114. Below the lower-most ring 110, a semicircular ring 118 for strength.

Figure 18:
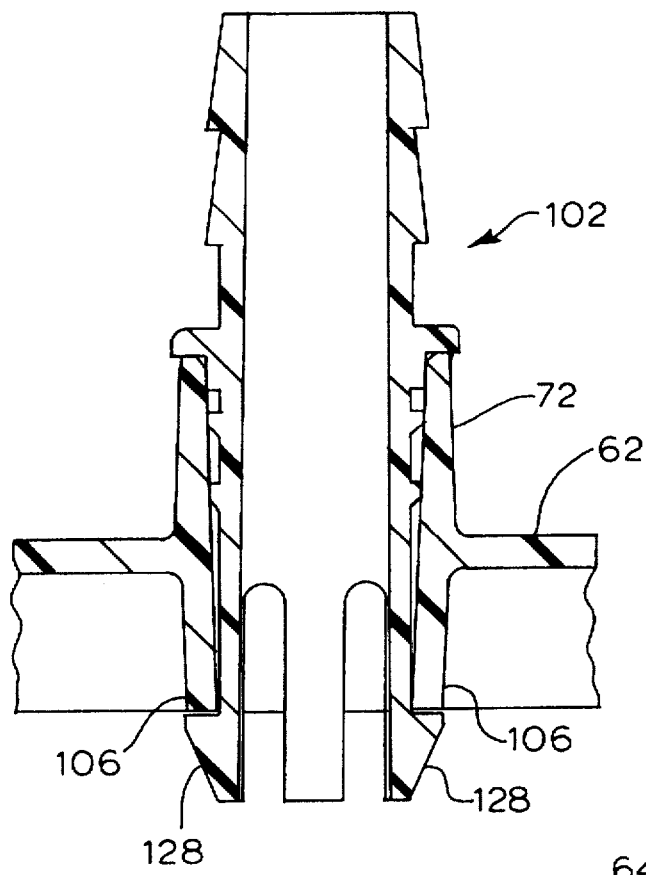
FIG. 18 is a cross-sectional view of the tandem tube connector attached to a canister lid through a tandem tube port.

The distal or innermost portion of the tandem connector body 108 terminates in a plurality of legs 120 for passing through the tandem port when the connector is connected to the tandem port. Preferably, four equally, circumferentially spaced legs are positioned around and form the inside terminal end of the tandem connector. Each leg has a preferably uniform wall thickness except for outwardly extending catches or locks, the first two of which locks 122 are shown in FIG. 15 on the first pair of legs and the second two of which locks 124 are shown in FIG. 16 on the second pair of legs. The locks 122 and 124 extend outwardly to engage the inner-most rim of the tandem port, which rim 106 extends downwardly from the underside of the lid 62 (FIG. 18). Each lock includes a guide surface 128 for pushing the legs inward through the action of the outer rim of the tandem port when the tandem connector is first inserted into the tandem port. Each guide 128 terminates in a radially inwardly extending locking surface. The locking surface for the first ramp locks 122 are ramping or camming surfaces 130 extending radially inwardly and downwardly toward the body of the tandem connector. The locking surfaces for the straight locks 124 extend straight radially inwardly toward the tandem connector body.

Once installed, the tandem connector 102 is effectively fixed in the tandem port. If any removal force is applied to the tandem tube or connector, the camming surfaces 130 will bear against the lower rim of the tandem port, thereby camming the corresponding first pair of legs 120 inwardly until the two legs in the pair meet. Because of the angled surfaces 130, the first pair of legs 120 are bent inwardly before the second pair of legs 120 begin to bend inwardly through any action of the rim of the tandem port. Moreover, any bending of the second pair of legs 120 will cause them to contact the other pair of legs, preventing any further inward bending of the legs. The ramped locks 122 are dimensioned so that the outer edges of the ramped locks will still engage the rim of the tandem port even when the innermost points of the first pair of legs 120 would be touching along the center line, because of bending at the bending points 134. Additionally, the guides for the straight locks 124 are dimensioned so that they still engage the rim of the tandem port even when they are bent inwardly to contact the first pair of legs. As a result, no amount of force will unlock the legs from the rim of the tandem port, without destroying the connector itself. It should be noted that the connector can still be inserted into the tandem port and locked since the bending upon such insertion takes place at the point where the legs join the rest of the tandem connector body 108 rather than solely at the point where the ramped locks 122 and straight locks 124 join the connector legs.

In an alternative embodiment (not shown), legs 120 having locks 122 and 124 are replaced a barb similar to ribs 104 (FIG. 16). Rim 106 has notches (not shown) running vertically from rim 106 to the underside of lid 62, allowing rim 106 to spread slightly until the barb has passed rim 106, wherein the edges of rim 106 spring back to positively lock tandem connector 102 into place. This alternative embodiment would prevent legs 120 from occluding the tandem port 72 should operating room personnel fail to seat tandem connector 102 into tandem port 72.

In the preferred embodiment, a tandem tube connector having an internal radius at the legs of approximately 0.323 inches and an internal radius at the opposite end of approximately 0.290 inches has a thickness for the legs of approximately 0.400 inches and an outside diameter at the points of the ramped locks 122 of 0.573 inches and an outside diameter at the straight locks 124 of approximately 0.543 inches. The distance from the distal side of the rim 106 to the proximal-most point on the ramped locks 122 is preferably about 0.790, which is the same as the distance to the proximally-facing surfaces on the straight locks. Tolerances should be made to ensure proper seal between the tandem connector body and the port while still allowing the movement of the legs to maintain a stable lock. An alternative lock has the body extend completely to the end of the locking elements (filling the openings between the legs to form a complete cylinder) and reducing the radial size of the locks while still ensuring a stable lock and easy installation of the connector in the port while ensuring a proper seal.

The tandem tube valve 136 (FIGS. 10–14) permits two way fluid flow through the tandem tube when the tandem tube valve 136 is mounted to a patient port on a canister, but prevents fluid flow out of the valve when the valve is disconnected. The tandem tube valve substantially minimizes the possibility of contamination when tandem-connected canisters are disconnected, and while any given liner-lid combination is being disposed. The tandem valve is preferably placed in the portion of the tandem tube which is to be connected to a secondary canister since the habit of most technicians is to disconnect tandem tubes from the secondary canisters rather than from the primary canister. However, it should be understood that suitable valves can be placed at either end of the tandem tube to achieve the same purpose, especially if both ends of the tandem tube can be disconnected from their respective ports.

The tandem valve preferably includes a tandem valve housing top 138 and a bottom 140. The housing positions and retains a flapper valve 142 and a wiper valve 144, having a wall 145 defining an opening for the riser portion of the patient port, separated by a valve spacer 146. These elements will be described more fully below.

Figure 11:
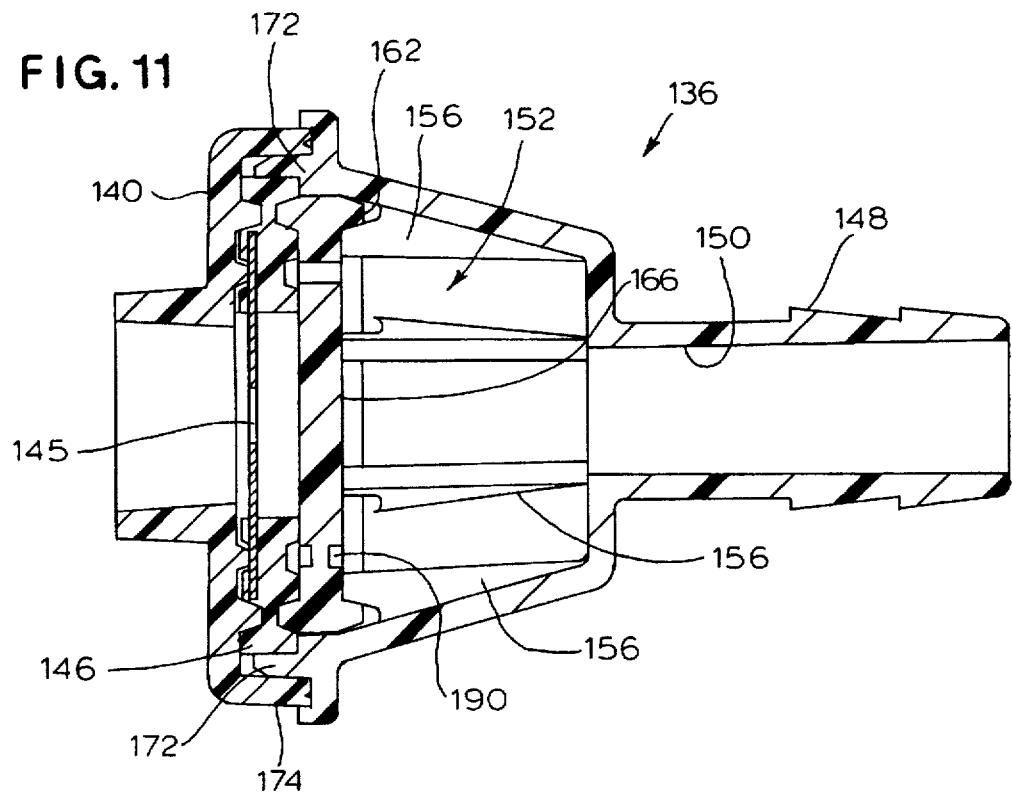
FIG. 11 is a cross-sectional view of the tandem tube valve of FIG. 10 in assembled form.

The housing top 138 includes one or more ribs 148 for frictionally engaging the other end of the tandem tube 100. The ribbed portion of the housing defines a passageway 150 through which fluid may pass from the tandem tube into the secondary canister. The passageway terminates in the interior 152 of the housing top 138. In longitudinal cross-section, the interior of the housing is substantially trapezoidal in shape with the narrower portion adjacent the passageway 150 and the wider portion at an opening 154 for the housing top. A plurality of supporting ribs 156, preferably eight, are uniformly distributed around the inside circumference of the trapezoidal housing portion and diverge slightly from the narrow portion of the housing to the opening 154. The ends 158 of the supporting ribs are spaced from the adjacent wall to form recesses 160 for receiving an outer circumferential wall 162 on the flapper valve 142 (FIG. 11). The spaced ends 158 engage a support surface 164 on the flapper valve interior to the wall 162 and exterior to the moveable valve element 166 of the flapper valve. The trapezoidal housing portion provides sufficient space for the moveable valve element 166 to move into the housing to permit fluid flow past the flapper valve from the tandem tube into the secondary canister.

The flapper valve fits within a bore 168 in the opening 154 and is held in place by the spacer 146 (FIG. 11). The wiper valve 144 fits against the opposite side of the spacer 146 and is sandwiched in place by the bottom portion 140 of the tandem valve housing.

The spacer fits into a counterbore 170 in the opening 154 of the top housing. The counterbore 170 is formed in an end wall 172 of the top housing which is angled to accept the mating bottom housing portion 140. The outer circumferential wall 174 of the bottom housing portion 140 engages a circular channel 176 formed outside of the end wall 172 so that the top and bottom housing portions may be welded or otherwise bonded and sealed.

The flapper valve 142 is preferably substantially symmetrical about a plane intersecting the central axis of the flapper valve thereby forming a plane to which the central axis is normal. The wall portion 162 is part of a short cylindrical outer wall 178 surrounding a ring portion 180. The supporting surface 164 on one side of the ring portion engages the ends 158 on the blades 156. On the opposite side, surface 182 and surface 184 engage mating portions 186 of the spacer 146. Flapper valve 142 is thereby sandwiched between the spacer 146 and the top housing 138.

The moveable valve element 166 is coupled to and supported by the ring portion 180 by a primary web 190.

Spacer 146 (FIG. 10) is also preferably symmetrical about a plane to which the center axis of the spacer is normal. The spacer preferably has a wall 194 defining an opening 196 through which the cone or riser of the patient port of the secondary canister is inserted to engage and open the valve element of the flapper valve in the valve housing. On the flapper valve side of the spacer, an inner groove 200 as well as the wall 194 define the valve seat 202 against which the valve element 166 seats when the tandem tube valve is removed from the mating port.

On the wiper valve side of the spacer, the spacer again has a first outer groove 204 for engaging a corresponding circular ridge 206 in the inside of the bottom housing 140. The inward adjacent circular ridge 208 on the spacer engages the groove 210 to sandwich the wiper valve 144 between circular ridge 212 on the spacer and circular ridge 214 on the bottom housing. Preferably, the groove 210 and the corresponding ridge 208 capture part of the wiper valve to hold it in place.

Figure 12:
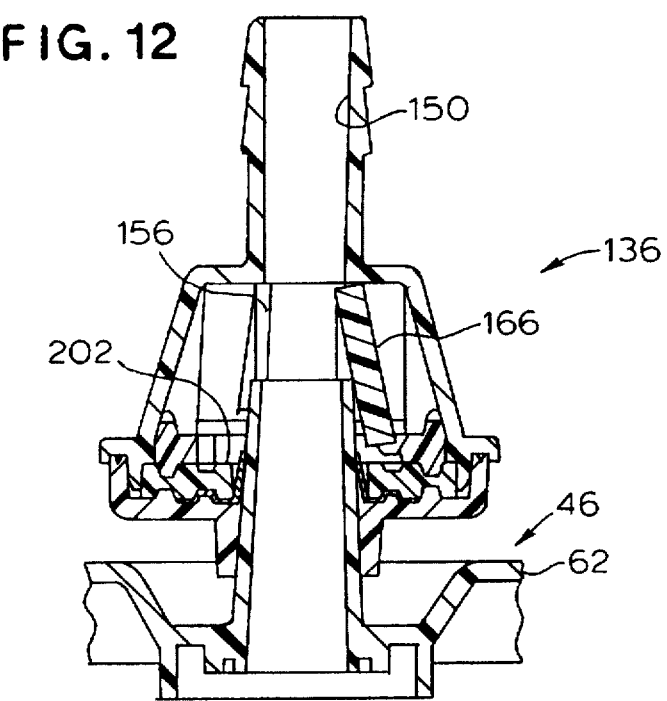
FIG. 12 is a tandem tube valve in place on the patient port of a downstream canister with the flapper valve held open by the patient port on the downstream lid.
Figure 13:
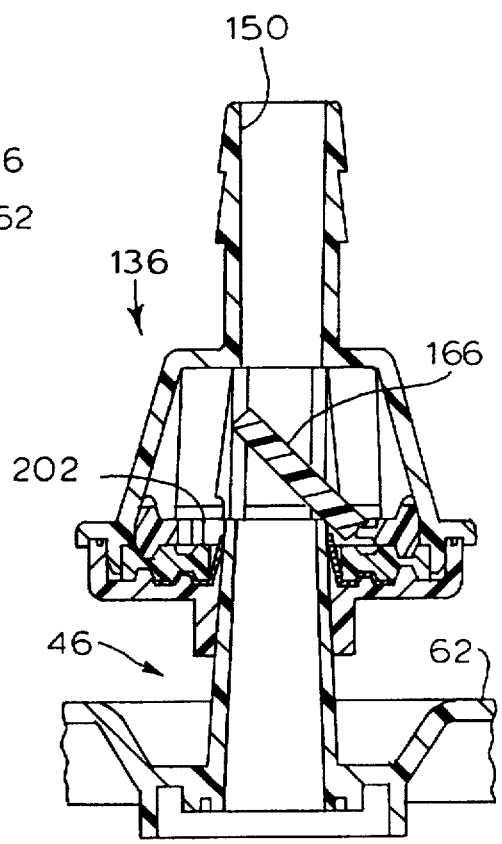
FIG. 13 is a cross-sectional view similar to that of FIG. 12 showing the tandem tube partially removed from the patient port and showing the flapper valve partially closed and the wiper valve contacting the wall of the port.
Figure 14:
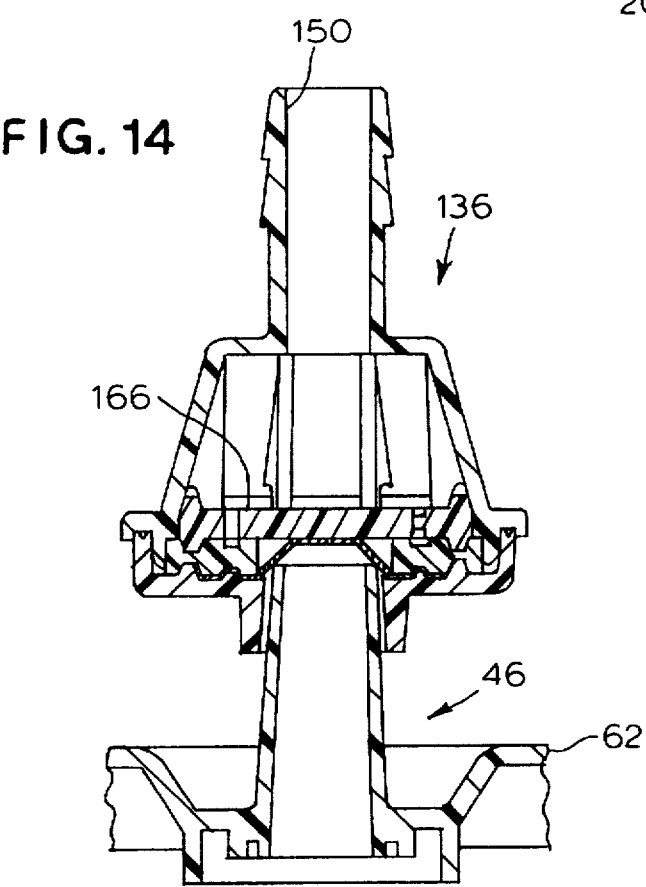
FIG. 14 is a cross-sectional view of the tandem tube valve similar to that of FIG. 12 with the valve being further removed and the wiper valve in contact with the mating port.

FIGS. 12–14 demonstrate the operation of the tandem valve. In FIG. 12, the tandem valve is fully seated on its corresponding patient port so that the riser of the patient port holds the moveable valve element of the flapper valve open permitting fluid flow from the tandem tube into the canister in accordance with the proper pressure differential. Additionally, the opening 145 in the wiper valve 144 elastically surrounds the riser. In FIG. 13, the tandem valve is partially removed from its corresponding riser and the moveable valve element of the flapper valve follows the top of the riser as the riser is removed from the tandem valve housing. The opening in the wiper valve 144 slides along the riser as the riser is removed wiping any fluid in front of it. Finally, in FIG. 14, the moveable valve element of the flapper valve is seated on the valve seat 202 and the wiper valve is almost completely removed from the riser.

With the tandem valve, further flow of fluid from the tandem tube outward of the tandem valve is prevented once the tandem tube is disconnected from its associated tandem port. Any fluid within the tube is retained therein or falls back into its primary canister. The valve operates regardless of whether or not removal of the tandem tube valve is intentional or accidental.

A tandem tube valve cap 216 (not shown) is retained on the tandem tube so that the opening on the tandem tube valve housing can be capped at any time. After being capped, the tandem tube is fully sealed between the cap and the liner of the lid-liner combination to which the tandem tube is connected.

In the preferred embodiment, the canister lid, connectors and ports are formed from high density polyethylene. The liner is preferably formed from low density polyethylene and the tandem tube connector is preferably formed from a polypropylene homopolymer. The port caps such as the tandem tube valve cap are preferably formed from low density polyethylene. The valve housing is preferably formed from styrene, as is the tandem valve spacer, while the flapper valve is preferably formed from natural or synthetic polyisoprene and the wiper valve is preferably formed from natural pure gum rubber. The opening 145 in the wiper valve 144 is preferably 0.125 inch for a minimum outside patient port diameter of 0.361 inch.

In accordance with one aspect of a patient port for use with the present invention (FIG. 20), the patient suction port 300 is preferably on the lid for the container for receiving fluids and includes a wall 301 defining a port opening and an upper rim 304 on the wall. The wall of the port also preferably includes at least one wall 303 defining a passageway from a first side of the patient port to a second side of the patient port for allowing a fluid such as air under a pressure differential such as a vacuum to pass from one side of the wall of the patient port to the other side of the wall to thereby minimize any pressure differential between the two sides. The passageway preferably takes the form of three grooves, discontinuities or scallop-like portions 302 formed in or near the top rim 304 of the port. Preferably the grooves are spaced substantially equidistant around the circumference of the rim and are formed from curved surfaces depending from the rim to flat surfaces at the bottoms of the grooves. The groove bottoms need not be flat, however.

The grooves minimize the possibility, when the connector of the patient tube or of a tandem tube is insufficiently placed onto or over the patient port, that the natural rubber disc of the flapper valve is pulled down by the pressure differential across the flapper valve onto the rim of the patient port. Such a position is depicted in FIG. 21 and could occur if the passageways are not included in the wall of the patient port. If the flapper valve disc covers the port by contacting the rim and there are no passageways to decrease any rise in pressure difference, the vacuum cannister system could shut down or fail to properly operate. The position of the valve in FIG. 21 is exagerated and would not occur where the passageways through the wall are provided. With the passageways, the flapper valve would preferably be in the position it would take if there were no suction at all in the system.

In FIG. 21, the tube connector and valve 306 is insufficiently pressed only part of the full way down onto patient suction port 300. Were tube valve 306 to be properly seated all the way down onto patient suction port 300, flapper valve 308 would be fully open, as shown in FIG. 12. However, because tube valve 300 is not positioned all the way down, flapper valve 308 is only partially opened. Flapper valve 308 is preferably made of an elastomeric material such as natural rubber. Because preferred materials for the flapper valve 308 are soft and flexible, flapper valve 308, in its partially open position as shown in FIG. 13, is capable of being forced against the upper rim 304 of patient suction port 300 by the pressure differential created by suction vacuum. In the absence of the grooves 302, flapper valve 308 would be forced down toward the upper rim 304, and air could cease to flow through the system.

With the grooved patient suction port, grooves 302 allow air to flow in the gaps or interstices defined by the grooves 302. The interstices are preferably large enough that an insufficient pressure differential can be created between tube valve inner volume 310 and patient suction port main passageway 312 to force and hold flapper valve 308 down onto upper rim 304. The interstices therefore not only allow air and fluid to flow between them, but also prevent flapper valve 308 from closing over the rim. Thus, the apertured rim of patient suction port 300 allows sufficient air flow through the vacuum canister system, even though the tube valve 306 has not been fully placed onto patient suction valve 300.

In a system using a flapper valve comprised of natural rubber and a patient suction valve of 0.29 inches (0.25 cm) at its end distal of the cover, preferred results were obtained using a groove depth of 0.1 inches, (0.25 cm) a groove curve radius of 0.1 inches, (0.25 cm) and an interstitial distance of 0.068 inches (0.17 cm) measured from the end of one scallop to the beginning of an adjacent scallop.

It is not necessary that the unevenness or discontinuities on upper rim 304 of patient suction port 300 be scalloped. Interstices could alternatively be formed with walls having right angles or any other shape. However, scallops are preferred because right angles or other sharp edges at upper rim 304 could damage or cause hang up of the flapper valve 308, especially at the time that tube valve 306 is being seated onto patient suction port 300.

Other types of air passageways could also be formed into the walls of patient suction port 300 that would accomplish the same purpose as interstices between the scallop edges. For example, suction port 300 could have round holes, rectangular notches, or other passageways in it just below upper rim 304. Such passageways and variations thereon are fully contemplated as being within the scope of the present invention. However, a scalloped upper rim is preferred for ease of manufacturing.

The underside of or side of the tandem port internal to the cannister may have slits in it to accomodate a tandem tube connector which does not have discreet legs but only a circumferential, outwardly extending shoulder on the end portion of the tandem tube connector. The shoulder will engage the slotted end of the underside of the tandem tube port or spout so that the tandem tube cannot be removed from the lid once properly inserted. The slotted end on the port allows the wall to expand outward slightly as the shoulder portion of the connector passes to the end of the passageway and out the end of the tandem spout to engage the end surface of the spout.

A vacuum canister fluid collection system and its components have been described and which will minimize the possibility of reflux or loss of fluid upon removal of vacuum, thereby minimizing the possibility of contamination or injury. Additionally, the possibility of contamination through accidental removal of caps on ports or loss of vacuum is also minimized. The system is designed so that full canisters will have their lids unsealed and disengaged from the canister upon removal of vacuum to minimize any possible pressure differential between the liner and atmospheric pressure. Preexisting pressure differentials and components are beneficially used to accomplish this result.

Although the present invention has been described in detail with reference only to the presently preferred embodiments, it will be appreciated by those of ordinary skill in the art that various modifications can be made without departing from the spirit of the invention. Accordingly, the invention is limited only by the following claims.

What is claimed is:

1. A suction cannister system comprising:
   a container for receiving fluids having a wall defining an opening therein and further having an inside and an outside;
   a cover for the container for sealing the opening in the container;
   a suction port associated with at least one of the container and the cover;
   a port in at least one of the container and the cover for providing a passageway between the inside of the container and the outside of the container, the port including a port wall extending longitudinally to a port rim defining a port opening for providing the passageway between the inside and the outside, the port wall also including a first side external to the passageway, a second side within the passageway and a surface which defines a passageway from the first side of the port wall to the second side of the port wall; and
   a connector for connecting the port to a tube, the connector including a first portion adapted to be placed over the port and engage the side of the port external to the passageway.

2. The suction cannister system of claim 1 wherein the port rim defines the surface such that a fluid such as air is allowed to pass below the rim and from the first to the second sides of the port wall.

3. A suction cannister comprising:
   a container for receiving fluids having a wall defining an opening therein and further having an inside and an outside;
   a cover for the container for sealing the opening in the container;
   a suction port associated with at least one of the container and the cover; and
   a port in at least one of the container and the cover for providing a passageway between the inside of the container and the outside of the container, the port including a port wall extending longitudinally to a port rim defining a port opening for providing the passageway between the inside and the outside, the port wall also including a first side external to the passageway and a second side within the passageway and wherein the port wall includes three notches substantially equally spaced around the rim which define passageways from the first side of the port wall to the second side of the port wall.

4. The suction cannister of claim 3 wherein the notches are rounded.

5. The suction cannister of claim 4 wherein each notch includes oppositely facing rounded sides connected by a relatively flat surface at the bottom of the respective notch.

6. The suction cannister of claim 5 wherein each notch is connected to an adjacent notch by a flat rim surface extending from a respective rounded side of one notch to a rounded side of an adjacent notch.

7. A suction fluid collection system comprising:
a fluid collection reservoir;
a cover for said reservoir;
a suction port associated with at least one of the reservoir and the cover;
a port in said cover, said port including a port wall extending longitudinally from the cover and having an interior side defining a passageway, an exterior side and a top rim, said top rim defining a gap through said port wall; and
a connector for connecting the port to a tube, the connector including a first portion adapted to be placed over the port and engage the exterior side.

8. The suction fluid collection system of claim 7 wherein said gap is sufficiently large as to allow air to pass therethrough when an air pressure differential is applied across said gap.

9. The suction fluid collection system of claim 8 wherein the gap is sufficiently large to prevent a flapper valve biased away from the top rim from being sucked against the top rim.

10. The fluid collection system of claim 7 wherein said top rim is rounded.

11. The suction fluid collection system of claim 7 wherein the gap is defined by a rounded wall.

12. A suction fluid collection system comprising:
a fluid collection reservoir;
a cover for said reservoir;
a suction port associated with at least one of the reservoir and the cover;
a port on said reservoir, said port including a port wall having an inside face defining a passageway and an outside face, said port wall having a passage from said inside face to said outside face; and
a connector for connecting the port to a tube, the connector including a first portion adapted to be placed over the port and engage the outside face.

13. A suction fluid collection system comprising:
a fluid collection reservoir;
a cover for said reservoir; and
a port in said cover, said port including a port wall extending longitudinally from the cover and having a top rim, said top rim defining a plurality of gaps defined by a rounded wall, each gap including oppositely facing sides having upper portions that are rounded and wherein the sides of a respective gap are connected by a flat surface at the bottom of the gap.

14. The suction fluid collection system of claim 13 wherein each gap is connected to an adjacent gap by a flat rim surface extending from a respective rounded side of one gap to a rounded side of an adjacent gap.

15. A suction fluid collection system comprising:
a fluid collection reservoir;
a cover for said reservoir;
a first port in said cover, said first port including a port wall extending longitudinally from the cover and having a top rim, said top rim defining a gap through said port wall;
a second port in the cover;
a tube extending from the second port;
a connector for connecting the tube to a first port in a second fluid collection reservoir while in a position of full engagement, the connector including:
a first portion defining a first opening for engaging the first port in the second fluid collection reservoir;
a second portion for engaging the tube; and
a sealing member in the connector configured to seal the first opening when the connector is completely disengaged from the first port, and to move away from the first opening when the connector is at least partially engaged with the first port.

16. The suction fluid collection system of claim 15 wherein the connector further includes a wiper valve for reducing any loss of fluid when the connector is disengaged from the first port of the second fluid collection reservoir.

17. The suction fluid collection system of claim 15 wherein the sealing member is a flapper valve.

18. The suction fluid collection system of claim 17 wherein the first portion of the connector has a wall defining the first opening which accepts the first port and wherein the flapper valve is adjacent the wall.

19. The suction fluid collection system of claim 17 wherein the flapper valve includes a flat surface facing outwardly of the connector and wherein the top rim of the port includes at least one substantially flat surface for engaging the flat surface on the flapper valve to open the flapper valve when the connector is at least partially engaged with the port.

20. A suction cannister comprising:
a container for receiving fluids having a wall defining an opening therein and further having an inside and an outside;
a cover for the container for sealing the opening in the container;
a suction port associated with at least one of the container and the cover;
a port in at least one of the container and the cover for providing a passageway between the inside of the container and the outside of the container, the port including a port wall extending longitudinally to a port rim defining a port opening for providing the passageway between the inside and the outside, the port wall also including a first side external to the passageway and a second side within the passageway and a surface which defines a passageway from the first side of the port wall to the second side of the port wall, the surface being in spaced relation to and distinct from the port rim.

21. A suction fluid collection system comprising:
first and second fluid collection reservoirs;
a port on the second reservoir, the port having a wall including an interior face defining a passageway, an exterior face and a gap extending from the interior face to the exterior face located and configured such that a substantially planar surface is incapable of simultaneously blocking both the passageway and the gap; and a fluid conduit engaged with both the first reservoir and the port on the second reservoir for establishing fluid communication therebetween, the fluid conduit including:
- a closeable valve in the fluid conduit, wherein the closeable valve is held open when the fluid conduit is fully engaged with the port on the second reservoir; and
- a wiper valve for substantially preventing loss of fluid upon disconnection of the fluid conduit.

22. A suction cannister comprising:

a container for receiving fluids having a wall defining an opening therein, an inside and an outside;

a container cover for sealing the opening in the container;

a suction port associated with at least one of the container and the cover; and a port in at least one of the container and the cover for providing a passageway between the inside of the container and the outside of the container, the port including a port wall extending longitudinally to a port rim defining a port opening for providing the passageway between the inside and the outside of the container, the port wall including a first side external to the passageway and a second side within the passageway and the rim including at least one surface which defines a passageway from the first side of the port wall to the second side of the port wall, the at least one surface defining a first width at an open longitudinal end and a second width at a closed longitudinal end, the first width being substantially greater than the second width.

23. A suction fluid collection system comprising:

a fluid collection reservoir;

a cover for the reservoir;

a suction port associated with at least one of the reservoir and the cover;

a port in the cover, the port including a port wall extending longitudinally from the cover and having an interior side defining a passageway and an exterior side and;

means for providing a fluid passage from the exterior side of the port to the interior side of the port when a connector is placed over the port and engages the exterior side.

* * * * *